US009655786B2

(12) United States Patent
Piantoni et al.

(10) Patent No.: US 9,655,786 B2
(45) Date of Patent: May 23, 2017

(54) SEALING SYSTEM

(71) Applicant: GDM S.p.A., Bologna (IT)

(72) Inventors: Matteo Piantoni, Albino (IT); Valerio Soli, Bologna (IT)

(73) Assignee: GDM S.p.A., Bologna (IT)

( * ) Notice: Subject to any disclaimer, the term of this patent is extended or adjusted under 35 U.S.C. 154(b) by 0 days.

(21) Appl. No.: 15/109,686

(22) PCT Filed: Jan. 22, 2015

(86) PCT No.: PCT/IB2015/050491
§ 371 (c)(1),
(2) Date: Jul. 5, 2016

(87) PCT Pub. No.: WO2015/110983
PCT Pub. Date: Jul. 30, 2015

(65) Prior Publication Data
US 2016/0324695 A1  Nov. 10, 2016

(30) Foreign Application Priority Data

Jan. 24, 2014 (IT) .................................. BO14A0029

(51) Int. Cl.
*B32B 37/00* (2006.01)
*A61F 13/15* (2006.01)
(Continued)

(52) U.S. Cl.
CPC .. *A61F 13/15739* (2013.01); *A61F 13/15747* (2013.01); *B29C 65/086* (2013.01);
(Continued)

(58) Field of Classification Search
CPC ......... A61F 13/15739; A61F 13/15737; B29C 65/08; B29C 65/086; B29C 65/7894;
(Continued)

(56) References Cited

U.S. PATENT DOCUMENTS 5,552,013 A * 9/1996 Ehlert ............... A61F 13/15739
100/160
7,204,899 B2 * 4/2007 Van Eperen ...... A61F 13/15723
156/269

(Continued)

FOREIGN PATENT DOCUMENTS

EP        1726278 A1    11/2006

OTHER PUBLICATIONS

International Search Report and Written Opinion dated Jun. 11, 2015 for counterpart PCT Application No. PCT/IB2015/050491.

*Primary Examiner* — James Sells
(74) *Attorney, Agent, or Firm* — Timothy J. Klima; Shuttleworth & Ingersoll, PLC

(57) ABSTRACT

An ultrasonic sealing system in a machine for making composite webs in the production of absorbent sanitary articles includes a contact roller having an axis of rotation and including a central portion and a peripheral portion which is supported by the central portion and includes an outer surface forming the outer surface of the contact roller itself. The contact roller includes a sealing pattern on the outer surface of the peripheral portion and also includes springs acting between the central portion and the peripheral portion, which is supported by the peripheral portion by means of the springs.

8 Claims, 2 Drawing Sheets

(51) Int. Cl.
*B65B 25/14* (2006.01)
*B65B 51/16* (2006.01)
*B65B 51/22* (2006.01)
*B29C 65/08* (2006.01)
*B29C 65/78* (2006.01)
*B29C 65/00* (2006.01)
*B29L 31/48* (2006.01)

(52) U.S. Cl.
CPC ...... *B29C 65/7894* (2013.01); *B29C 66/1122* (2013.01); *B29C 66/436* (2013.01); *B29C 66/7294* (2013.01); *B29C 66/8161* (2013.01); *B29C 66/83511* (2013.01); *B65B 25/145* (2013.01); *B65B 51/16* (2013.01); *B65B 51/225* (2013.01); *A61F 2013/15869* (2013.01); *B29L 2031/4871* (2013.01); *B29L 2031/4878* (2013.01)

(58) Field of Classification Search
CPC ............... B29C 66/1122; B29C 66/436; B29C 66/7294; B29C 66/8161; B29C 66/83511; B65B 25/145; B65B 51/16; B65B 51/225
USPC .................................. 156/73.1, 580.1, 580.2
See application file for complete search history.

(56) References Cited

U.S. PATENT DOCUMENTS

| | | | |
|---|---|---|---|
| 7,866,361 B2* | 1/2011 | Bohm | B26D 1/0006 156/510 |
| 9,283,713 B2* | 3/2016 | Heeg | B29C 65/08 |
| 2006/0276320 A1* | 12/2006 | Aiolfi | B65B 63/045 493/441 |

* cited by examiner

SEALING SYSTEM

This application is the National Phase of International Application PCT/IB2015/050491 filed Jan. 22, 2015 which designated the U.S. and that International Application was published under PCT Article 21(2) in English.

This application claims priority to Italian Patent Application No. BO2014A000029 filed Jan. 24, 2014, which application is incorporated by reference herein.

TECHNICAL FIELD

This invention relates to a sealing system and, more specifically, to an ultrasonic sealing system in a machine for making composite webs in the production of absorbent sanitary articles.

BACKGROUND ART

In the sector of machines for manufacturing absorbent sanitary articles such as, for example, baby nappies, sanitary towels or the like, wide use is made of ultrasonic sealing systems.

As is known, nappies comprise an absorbent pad or padding which is normally enclosed between a permeable inner layer of non-woven fabric and an impermeable outer layer of polyethylene.

These pads are normally made from a composite web, that is, a multi-layer web, which is cut into lengths.

Absorbent pads of known type comprise, for example, an absorbent core in turn comprising an absorbent material, such as, for example, granules of superabsorbent polymer material (SAP), which may be inside a mixture of containment cellulose pulp (fluff) and absorbent material binder, sandwiched between two layers of non-woven fabric.

At least two layers of the nappy may be joined to each other by seals which are suitably made in such a way as to form, for example, a plurality of rows containing the absorbent material.

These seals can be made by means of ultrasonic systems which, in one embodiment, comprise a contact roller, also known as "anvil", having on its outer cylindrical surface a pattern of the sealing lines to be made on the finished product.

The layered composite web as described above, from which the nappies or parts thereof are obtained, is made to advance on the surface of the contact roller.

A sonotrode, energized by a source of energy, operates on the web on the side opposite to the anvil in such a way as to make the seals according to the pattern formed on the anvil itself.

In practice, the sonotrode produces friction between the parts of the suitably layered web by means of vibration at ultrasonic frequency opposed by the anvil, in particular at the sealing pattern formed on the anvil. This intense vibration produces heat which causes the materials involved to melt, thereby sealing and assembling the composite web.

One disadvantage of ultrasonic sealing systems of the type described is due to the fact that, in the specific case of absorbent sanitary articles, part of the absorbent material, usually in granular or similar form, inside the composite web may be located along the sealing lines. The seals along these lines are therefore not made properly and are not entirely reliable.

AIM OF THE INVENTION

In this context, the main purpose of this invention is to propose a sealing system which allows overcoming the above mentioned disadvantages.

This invention has for an aim to provide an ultrasonic sealing system in a machine for making composite webs in the production of absorbent sanitary articles which allows more reliable seals to be obtained.

The technical purpose and aims specified are substantially achieved by a sealing system comprising technical features as disclosed herein.

BRIEF DESCRIPTION OF THE DRAWINGS

Further features and advantages of this invention are more apparent in the non-limiting description of a preferred but non-exclusive embodiment of a sealing system, as illustrated in the accompanying drawings, in which.

DETAILED DESCRIPTION OF PREFERRED EMBODIMENTS OF THE INVENTION

With reference to the accompanying drawings, the numeral 1 denotes a contact roller according to this invention.

Figure 1:
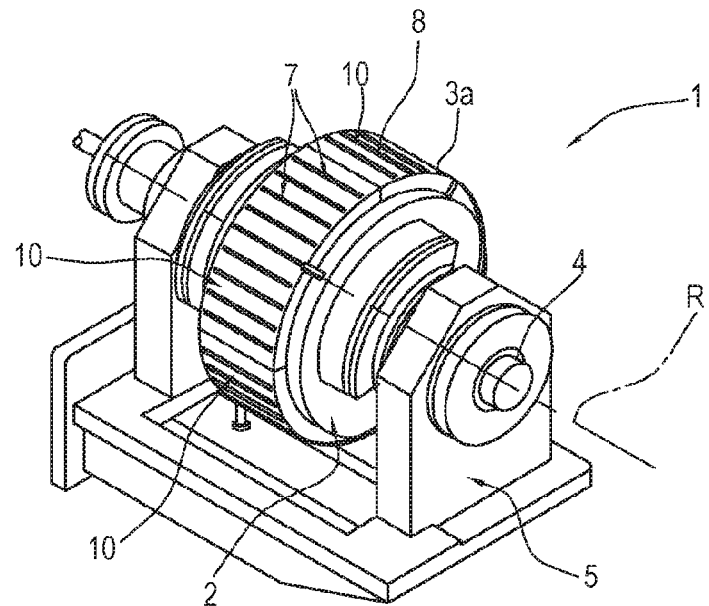
FIG. 1 shows a sealing system according to this invention in a schematic perspective view, with some parts cut away for better clarity.
Figure 2:
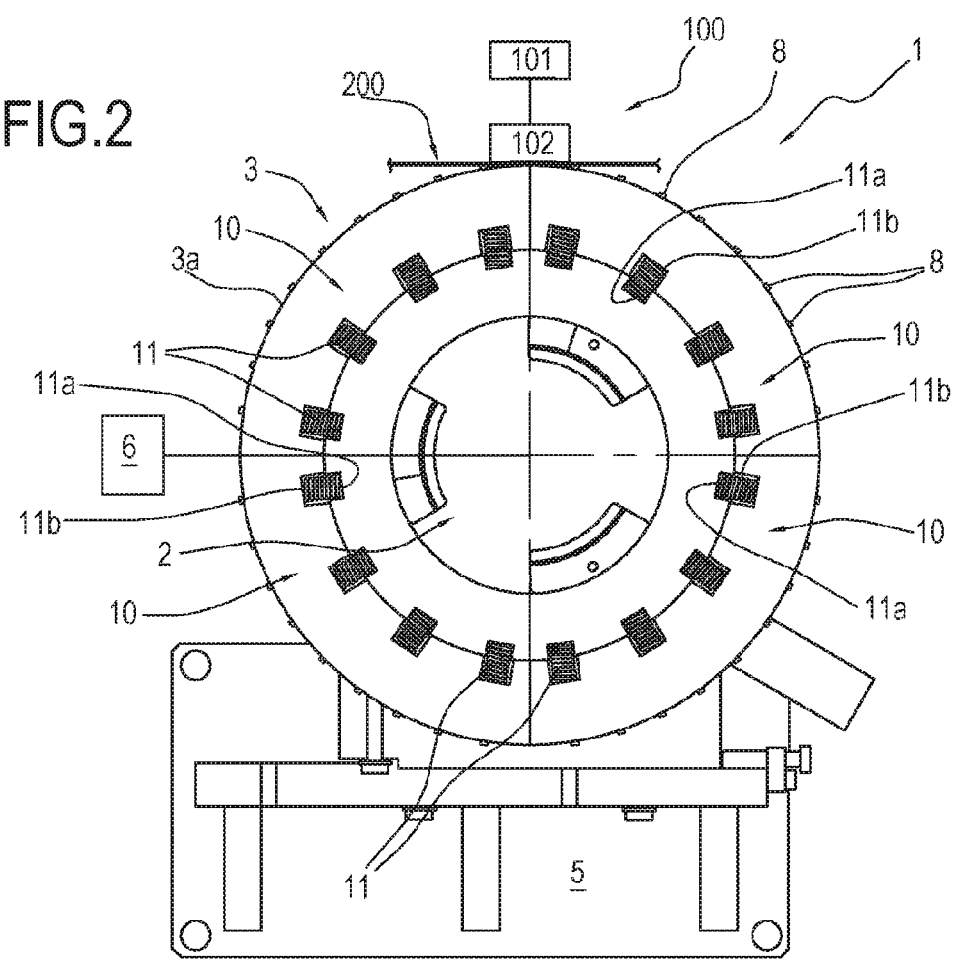
FIG. 2 shows the sealing system of FIG. 1 in a schematic transversal cross section with some parts represented in blocks.
Figure 3:
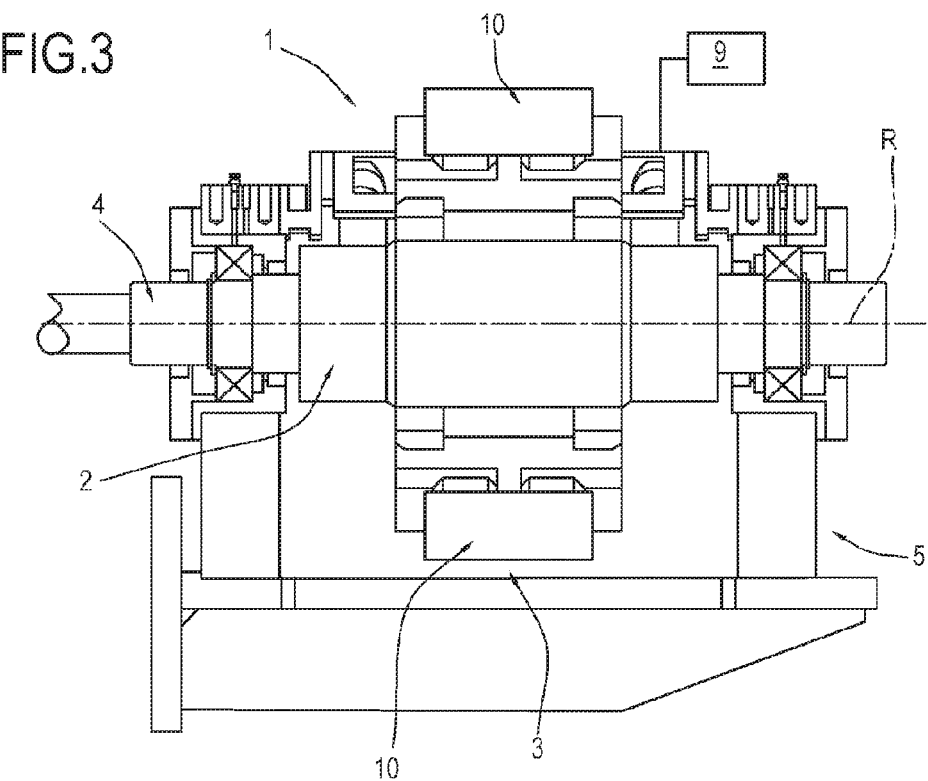
FIG. 3 shows the sealing system of FIG. 1 in a schematic longitudinal cross section with some parts represented in blocks.

The roller 1 is designed for an ultrasonic sealing system 100 of substantially known type and schematically represented in particular in FIG. 2.

Preferably, the roller 1 is designed for sealing systems 100 installed in machines for making composite webs in the production of absorbent sanitary articles such as, for example, baby nappies, to which express reference is hereinafter made, sanitary towels or the like.

Figure 4:
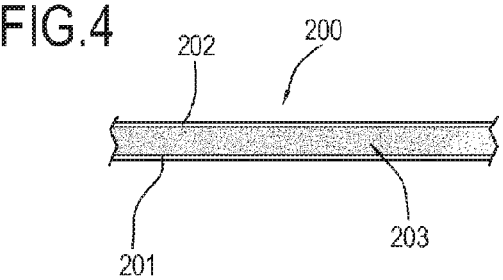
FIG. 4 is a schematic cross section of an example of a composite web obtainable with the sealing system of the preceding figures.

With reference to FIG. 4, the numeral 200 denotes a composite web used to make nappies not illustrated.

The nappies comprise an absorbent pad or padding which is normally enclosed between a permeable inner layer of non-woven fabric and an impermeable outer layer of polyethylene.

The web 200 is used, for example, to make the nappy padding and comprises an absorbent core sandwiched between two layers 201, 202 of non-woven fabric.

The absorbent core comprises an absorbent material 203, such as, for example, granules of superabsorbent polymer material (SAP) sandwiched between the layers 201, 202 of non-woven fabric.

In the finished nappy, the two layers 201, 202 of non-woven fabric are connected to each other by suitable seals.

The seals may, for example, form a plurality of cells for containing the absorbent material and they may be continuous or discrete, that is to say, they may be made according to different patterns, according to requirements.

These seals are made on the web 200 by means of the sealing system 100.

The sealing system 100 basically comprises an ultrasonic vibration energy source, represented as a block 101, a sonotrode, schematically represented as a block 102, in communication with the source 101 to transmit the vibration energy to the web 200 to be sealed and the aforementioned roller 1, also referred to as "anvil", which supports the web 200 and whose features are described only insofar as necessary for understanding this invention.

The roller 1 has an axis R of rotation and comprises a central portion 2 and a peripheral portion 3.

The central portion 2 comprises a shaft 4 by which the roller 1 is connected to a structure 5 which supports the roller 1.

The peripheral portion 3 is supported by the central portion 2 and has an outer surface 3a which forms the outer surface of the roller 1 designed to support the web 200 and against which the action of the sonotrode 102 is applied.

The roller 1 comprises a suction system, schematically represented as a block 6, in communication with the outer surface 3a of the peripheral portion so as to hold the composite web 200 against the roller 1.

The suction system 6 is of substantially known type and is not further described.

The contact roller 1 comprises a sealing pattern 7 on the outer surface 3a of the peripheral portion 3 which determines the sealing pattern of the web 200.

The sealing pattern 7 is in relief on the outer surface 3a of the peripheral portion, that is to say it is formed by a plurality of elements 8 which protrude in relief from the surface 3a, and which are suitably distributed over the surface 3a itself.

As illustrated in particular in FIG. 2, the contact roller 1 comprises suspension means, preferably elastic, acting between the central portion 2 and the peripheral portion 3.

Advantageously, the peripheral portion 3 is associated with the central portion 2 through the suspension means.

More precisely, the peripheral portion 3 is connected to the central portion 2 by a coupling system, schematically represented as a block 9.

A rotational motion imparted to the central portion 2 is transmitted to the peripheral portion 3 by means of the coupling system 9.

The peripheral portion 3 is connected to the central portion 2 by the suspension means which allow the peripheral portion 3 to move relative to the central portion 2 along a direction preferably transversal to the axis R of rotation.

The suspension means damp the vibrations imparted by the sonotrode 102 to the roller 1 during sealing.

Further, since the portion 3 is free to vibrate because it is not rigidly connected to the supporting structure 5, it also vibrates and thus adds to the vibrations imparted by the sonotrode 102.

In the preferred embodiment illustrated in the accompanying drawings, the peripheral portion 3 is made up of a plurality of sectors 10, four in the example illustrated, each associated with the central portion 2 through the coupling system 9 and the suspension means.

The sectors 10 are preferably independent of each other so that they can move relative to the central portion 2 independently of each other.

The sectors 10 form the portion 3 and are carried in rotation by the central portion 2.

As illustrated, the peripheral portion 3 is substantially a hollow cylinder, preferably formed by the sectors 10, whose outer surface constitutes the aforementioned surface 3a.

In practice, the central portion 2 is inserted in the cylinder and is connected thereto as described above, in particular by the coupling system 9 and the suspension means.

Looking in more detail at the suspension means, it may be observed that in the preferred embodiment illustrated by way of example, the suspension means comprise a plurality of elastic pushing elements 11 such as springs, for example, to which express reference is made herein but without limiting the invention.

Preferably, the line of action of the springs 11 is substantially radial, that is to say, it passes through the axis R of rotation of the roller 1.

In alternative embodiments not illustrated, the suspension means comprise pneumatic or hydraulic or even elastomer systems.

As illustrated, the suspension means comprise, for each spring 11, a housing 11a formed in the central portion 2 of the roller 1.

The suspension means comprise, for each spring 11, a housing 11b formed in the peripheral portion 3 of the roller 1.

Each housing 11a faces a corresponding housing 11b and the respective spring 11 contained in the space defined by the housings 11a and 11b.

In other words, the central portion 2 of the roller 1 has on its outer surface a plurality of housings 11a, each for a respective spring 11.

The housings 11b are formed in the inside surface of the peripheral portion 3 of the roller 1 and each faces a corresponding housing 11a in the portion 2.

Each elastic element 11 is held in a corresponding space formed by the portions 2 and 3 of the roller 1 at the housings 11a and the respective housings 11b.

The invention described brings important advantages.

In use, the web 200 is made to advance on the surface of the roller 1 which constitutes the anvil of the sealing system.

The portion 3 of the roller 1 which touches the web is made to vibrate by the sonotrode since it is suspended on the springs which allow the vibrating action to be suitably controlled. In the case of preferred use in the production of a web 200 of the type described above, for example, vibrating the portion 3 keeps material such as the absorbent material 203 clear of the elements 8 so it does not interfere with the action of the sonotrode which is therefore free to make optimal seals. In effect, at the seals, the layers of non-woven fabric remain in contact with each other without any extraneous bodies, such as the SAP, caught between them so that the resulting seals are free of imperfections.

The invention claimed is:

1. An ultrasonic sealing system in a machine for making composite webs in production of absorbent sanitary articles, comprising: a contact roller, said contact roller having an axis of rotation and comprising a central portion and a peripheral portion which is supported by said central portion, the peripheral portion including an outer surface forming an outer surface of said contact roller, said contact roller comprising a sealing pattern on said outer surface of said peripheral portion, said contact roller including a suspension system acting between said central portion and said peripheral portion, said peripheral portion being associated with said central portion by said suspension system.

2. The sealing system according to claim 1, wherein said peripheral portion comprises a plurality of sectors each associated with said central portion by a corresponding portion of the suspension system.

3. The sealing system according to claim 2, wherein the plurality of sectors are independent of one another.

4. The sealing system according to claim 1, wherein said suspension system comprises a plurality of elastic elements.

5. The sealing system according to claim 4, wherein said plurality of elastic elements each have a substantially radial line of action.

6. The sealing system according to claim 1, and further comprising a suction system in communication with the outer surface of said peripheral portion for holding a composite web fed by said contact roller.

7. The sealing system according to claim 1, wherein said peripheral portion is a hollow cylinder, a lateral surface of said hollow cylinder forming said outer surface of said peripheral portion, said central portion being inserted in said hollow cylinder.

8. The sealing system according to claim 1, wherein said sealing pattern is raised on said outer surface of said peripheral portion.

* * * * *